United States Patent [19]
Artz et al.

[11] Patent Number: 6,101,083
[45] Date of Patent: Aug. 8, 2000

[54] METHOD AND APPARATUS FOR REDUCING ELECTROSTATIC DISCHARGE DURING INTEGRATED CIRCUIT TESTING

[75] Inventors: Bruce Lloyd Artz, Walnutport; Edward P. Eberhardt, Slatington; Kenneth Phillips Moll, Allentown; Donna Robinson-Hahn, Center Valley, all of Pa.

[73] Assignee: Lucent Technologies Inc., Murray Hill, N.J.

[21] Appl. No.: 09/215,411

[22] Filed: Dec. 18, 1998

[51] Int. Cl.⁷ ........................................................ H05F 3/02
[52] U.S. Cl. .............................. 361/220; 73/865.6; 374/57
[58] Field of Search ...................... 361/212–220; 174/35 R, 35 MS; 374/45, 57; 206/709; 165/48.1, 61; 73/865.6; 324/453, 454

[56] References Cited

U.S. PATENT DOCUMENTS

| | | | |
|---|---|---|---|
| 4,316,231 | 2/1982 | Michel | 361/212 |
| 4,519,718 | 5/1985 | Staffin et al. | 374/45 |
| 4,779,163 | 10/1988 | Bickford et al. | 361/212 |
| 5,290,101 | 3/1994 | Englert et al. | 374/57 |
| 5,646,813 | 7/1997 | Jon et al. | 361/220 |

*Primary Examiner*—Fritz Fleming
*Attorney, Agent, or Firm*—Wendy W. Koba

[57] ABSTRACT

A method and apparatus for essentially eliminating ESD damage to integrated circuits being subjected to thermal shock testing includes the utilization of a static dissipative plastic carrier capable of withstanding high temperatures (e.g., 155° C.) and exhibiting a surface resistivity in the range of, for example, $10^{10}$–$10^{12}$ $\omega/\square$. Such a static dissipative plastic support structure will therefore eliminate static buildup during integrated circuit testing and prevent ESD damage to the circuits.

28 Claims, 2 Drawing Sheets

METHOD AND APPARATUS FOR REDUCING ELECTROSTATIC DISCHARGE DURING INTEGRATED CIRCUIT TESTING

BACKGROUND OF THE INVENTION

The present invention relates to a method and apparatus for reducing electrostatic discharge (ESD) during testing of integrated circuits and, more particularly, to a method and apparatus for virtually eliminating ESD damage during temperature cycling and thermal shock testing of integrated circuits.

Temperature cycling and thermal shock testing are two types of test performed on most integrated circuits (as well as circuit boards) during an initial "design qualification" (i.e., "prove-in") of the device or board. The testing may be accomplished by placing the item to be tested (i.e., the device or board) in a highly conductive, stainless steel perforated basket that is alternately subjected to extreme "hot" and "cold" baths, with high circulation to insure a uniform temperature within the bath. The temperatures may be, for example, 155° C. and −65° C., respectively, for the baths. In a typical test arrangement, the item being tested may be alternated up to 1000 cycles between the two temperatures. Submersion time at a particular temperature may be, for example, 15 minutes per cycle.

The bath itself may comprise chemicals such as liquid nitrogen, water, or a commercially available liquid such as Flourinet. One problem present in the prior art testing arrangement is the static potential created during the testing as a result of factors such as the chemical's resistance, the duration of the test, the rate of circulation and humidity within the test chamber. Static-sensitive integrated circuit devices may be exposed to as much as 10,000 volts during a typical thermal shock or temperature cycling operation.

Temperature cycling tests may also involve "air-to-air" (or any other gaseous environment) testing, using a pair of chambers maintained at two predetermined temperature extremes (such as 155° C. and −65+ C.). Electrostatic potential will also build up in this environment, with the capability to severely damage the parts being tested. "Thermal shock" testing may be defined as quickly changing the ambient temperature of the part being tested. Again, thermal shock testing results in the build up of static charge within the structure supporting the device being tested.

Prior attempts to reduce ESD damage to items being tested have included using alternative chemicals, or modifying the testing apparatus to reduce the circulation of the bath. Neither of these proposed solutions has been successful in reducing the static potential (and hence the ESD damage) to an acceptable level.

SUMMARY OF THE INVENTION

The need remaining in the prior art is addressed by the present invention, which relates to a method and apparatus for reducing electrostatic discharge (ESD) during testing of integrated circuits/boards (hereinafter referred to as "components") and, more particularly, to a method and apparatus for virtually eliminating ESD damage during temperature cycling and thermal shock testing of integrated circuit components.

In accordance with the present invention, the metallic test basket of the prior art is replaced with a high temperature, static dissipative plastic material having a surface resistivity in the range of, for example, $10^{10}$–$10^{12}$ $\omega/\square$. The plastic material is therefore able to eliminate any static buildup, as well as provide the high temperature stability required for tests involving temperature cycling between extremes (for example, a plastic that remains rigid to the upper extreme of 155° C.).

In one embodiment, the static dissipative plastic structure may comprise a basket (similar in design to prior art metallic baskets), with the components to be tested (i.e., individual circuits, circuit boards, or both) placed in the static dissipative plastic basket. In an alternative embodiment, the static dissipative plastic structure may formed as a tray for supporting a number of separate components so as to prevent movement of the individual components during testing. One arrangement of a tray structure of the present invention is capable of supporting "stacked" components.

It is an advantage of the present invention that a multiple number of items to be tested may be simultaneously loaded into the static dissipative basket or tray structure, thus reducing the testing time per device.

Other and further advantages of the present invention will become apparent during the course of the following discussion and by reference to the accompanying drawings.

BRIEF DESCRIPTION OF THE DRAWINGS

Referring now to the drawings.

DETAILED DESCRIPTION

Figure 1:
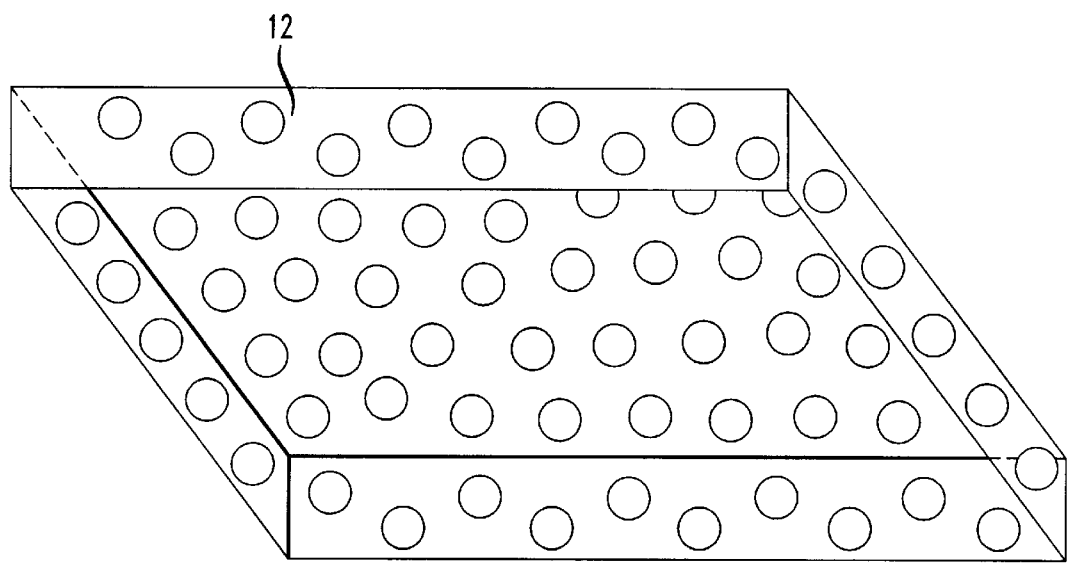
FIG. 1 illustrates an exemplary static dissipative plastic test basket for use in thermal testing of integrated circuit components in accordance with the present invention.

An exemplary static dissipative plastic basket 10 for handling integrated circuit devices/boards (hereinafter referred to as "components") being subjected to various temperature-based testing is shown in FIG. 1. In a preferred embodiment, basket 10 comprises a static dissipative plastic material with a surface resistivity in the range of, for example, $10^{10}$–$10^{12}$ $\omega/\square$ so as to eliminate electrostatic buildup during temperature cycling testing. Additionally, the static dissipative plastic material needs to remain mechanically stable over the entire temperature range of interest (an exemplary range being −65° C. to 155° C.). Static dissipative PTFE and static dissipative acetal (sold by DSM Engineering Plastic Products, Inc. as Semitron™ ESD 500 and Semitron™ ESD 225, respectively) have been found useful for these purposes. It is to be understood that any suitable engineering plastic exhibiting the requisite temperature and surface resistivity properties may also be used in accordance with the teachings of the present invention. As shown in FIG. 1, basket 10 includes a number of apertures 12. When basket 10 is used to temperature cycle components between liquid baths, apertures 12 allow for the bath liquid to enter basket 10 and completely surround the test components placed in the basket. During "air" temperature testing, the inclusion of apertures 12 result in a more uniform ambient temperature for the components being tested.

Figure 3:
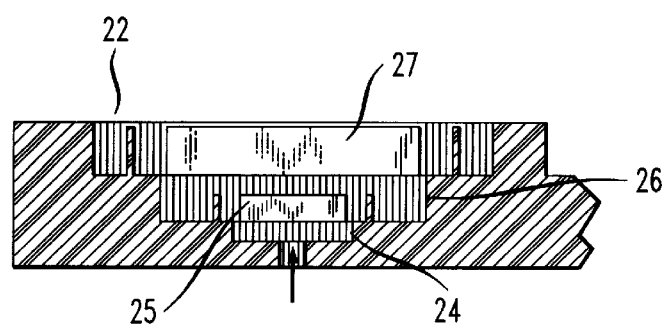
FIG. 3 is a cut-away side view of the exemplary tray of FIG. 2, taken along line 3—3, illustrating an exemplary ridge structure useful for stacking components within a tray.
Figure 2:
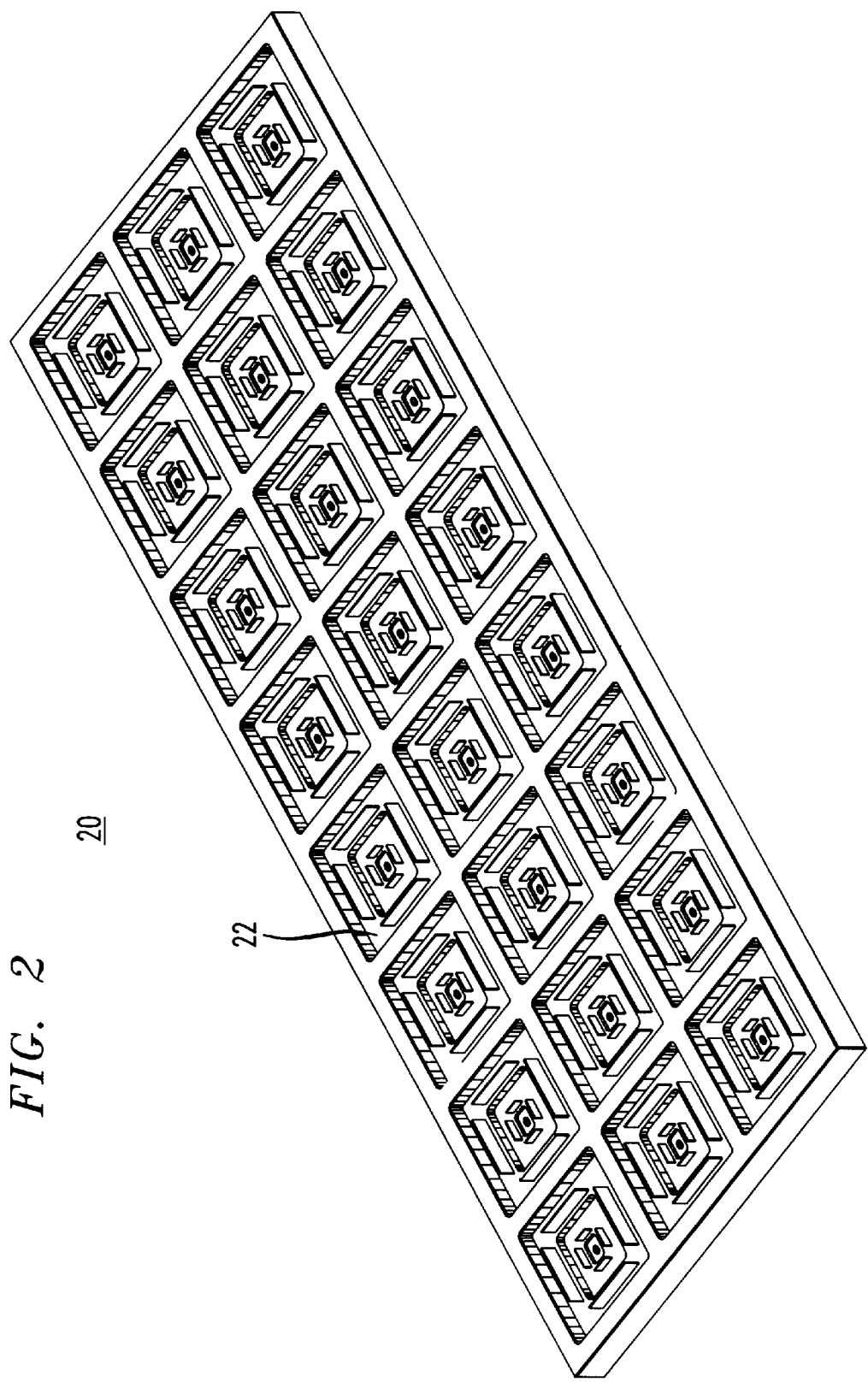
FIG. 2 illustrates an exemplary static dissipative plastic test tray for use in thermal testing of integrated circuit components in accordance with the present invention.

In most applications, the components being tested (either individual integrated circuits, circuit boards, or both) would simply be placed as "loose" items in basket 10. While this arrangement is suitable for certain applications, the movement of the components during testing may result in imparting additional damage to the components. FIG. 2 illustrates an exemplary static dissipative plastic test tray 20 that may be used to support the components being tested, while at the same time preventing damage related to the relative motion of the components during testing. Referring to FIG. 2, exemplary tray 20 is formed to include an 8×3 array of component cavities 22, where each cavity 22 is used to support a separate integrated circuit component (not shown). It is to be understood that this particular tray design is exemplary only, and a static dissipative plastic tray of the present invention may include any desired number of component cavities, disposed in any suitable pattern on the tray. In the exemplary embodiment of FIG. 2, each cavity 22 includes a number of support ridges, disposed at different depths within the cavity. A cut-away side view of an exemplary cavity 22 is illustrated in FIG. 3. As shown, cavity 22 includes a set of lower ridges 24 for supporting a first, relatively small component, such as component 25 shown in phantom in FIG. 3. A set of upper ridges 26 is also formed in cavity 22 and are used to support a second, larger component 27 (also shown in phantom). Thus, an advantage of tray 20 of the present invention is the capability to test two different-sized components at the same time, thereby doubling the test throughput by the capability of "stacking" a pair of components in a single cavity. An aperture 28 is included through the backside of cavity 22 so as to allow for a temperature equilibrium to be obtained during testing. Since, as shown in FIG. 3, upper component 27 remains below top surface 21 of tray 20, multiple trays may be stacked one upon the other during testing without causing unwanted physical contact between the individual components.

It is to be understood that the basket and tray designs discussed above are exemplary only and any static dissipative plastic structure having the requisite high temperature stability and surface resistivity characteristics is considered to fall within the spirit and scope of the present invention as defined by the claims appended hereto.

What is claimed is:

1. In a system for temperature testing an integrated circuit component by subjecting said component to relatively high and low temperature environments, apparatus for reducing electrostatic discharge during testing, said apparatus comprising a static dissipative plastic carrier for supporting said integrated circuit component during testing, said static dissipative plastic carrier exhibiting a relatively high surface resistivity and comprising a material capable of remaining mechanically stable during temperature cycling between the relatively high and low temperature environments.

2. In a system as defined in claim 1, the static dissipative plastic carrier further comprising a plurality of apertures to allow an ambient temperature environment to enter said static dissipative carrier and surround the tested integrated circuit.

3. In a system as defined in claim 2, wherein the ambient temperature environment comprises a gas.

4. In a system as defined in claim 2, wherein the ambient temperature environment comprises a liquid.

5. In a system as defined in claim 1, the static dissipative plastic carrier exhibiting a surface resistivity in the range of $10^{10}$–$10^{12}$ $\omega/\square$.

6. In a system as defined in claim 5, the static dissipative plastic carrier comprising static dissipative acetal.

7. In a system as defined in claim 5, the static dissipative plastic carrier comprising static dissipative PTFE.

8. A static dissipative plastic carrier for supporting an integrated circuit component during temperature testing, including temperature cycling between a first, relatively low temperature and a second, relative high temperature, said static dissipative plastic carrier exhibiting a relatively high surface resistivity and comprising a material capable of remaining mechanically stable during temperature cycling between the first and second temperatures.

9. A static dissipative plastic carrier as defined in claim 8 wherein said carrier exhibits a surface resistivity in the range of $10^{10}$–$10^{12}$ $\omega/\square$.

10. A static dissipative plastic carrier as defined in claim 8 wherein said carrier comprises a basket for containing a plurality of integrated circuit components during temperature testing.

11. A static dissipative plastic carrier as defined in claim 10 wherein said basket includes a plurality of apertures to enhance atmospheric flow around the integrated circuit components.

12. A static dissipative plastic carrier as defined in claim 8 wherein said carrier comprises a tray for supporting a plurality of separate integrated circuit components in a manner such that said components remain physically separated during testing, said tray defined as comprising a top major surface and a bottom major surface.

13. A static dissipative plastic carrier as defined in claim 12 wherein the tray includes a plurality of separate cavities formed through the top major surface, said cavities sized to allow for a separate integrated circuit component to be located in each cavity.

14. A static dissipative plastic carrier as defined in claim 13 wherein each cavity further includes an aperture formed through the bottom major surface of said tray.

15. A static dissipative plastic carrier as defined in claim 13 wherein each cavity is formed to include a first set of lower ridges for supporting a relatively small integrated circuit component and a second set of upper ridges for support a relatively larger integrated circuit component so that each cavity is capable of supporting two separate integrated circuit components during testing.

16. A static dissipative plastic carrier as defined in claim 8 wherein said static dissipative plastic carrier comprises static dissipative acetal.

17. A static dissipative plastic carrier as defined in claim 8 wherein said static dissipative plastic carrier comprises static dissipative PTFE.

18. A method for thermal testing an integrated circuit component, the method comprising the steps of:

a) providing a first low temperature environment;

b) providing a second high temperature environment;

c) loading the integrated circuit component into a static dissipative plastic carrier;

d) placing the loaded carrier in the first low temperature environment for a predetermined period of time;

e) placing the loaded carrier in the second high temperature environment for a predetermined period of time;

f) repeating steps d) and e) for a predetermined number of cycles.

19. The method as defined in claim 18 wherein the first, low temperature is approximately −65° C.

20. The method as defined in claim 18 wherein the second, high temperature is approximately 155° C.

21. The method as defined in claim 18 wherein in performing step a), a liquid bath environment is provided.

22. The method as defined in claim 21 wherein in performing step a), a liquid bath of liquid nitrogen is provided.

23. The method as defined in claim 18 wherein in performing step c), the integrated circuit is loaded into a static dissipative plastic carrier exhibiting a surface resistivity in the range of $10^{10}$–$10^{12}$ ω/□.

24. The method as defined in claim 23 wherein in performing step c), a plastic carrier comprising static dissipative acetal is provided.

25. The method as defined in claim 18 wherein in performing step c), a plastic carrier comprising static dissipative PTFE is provided.

26. The method as defined in claim 18 wherein in performing step d), the integrated circuit is submersed for approximately 15 minutes.

27. The method as defined in claim 26 wherein in performing step e), the integrated circuit is submersed for approximately 15 minutes.

28. The method as defined in claim 18 wherein in performing step f), the submersions are performed for approximately 1000 cycles.

* * * * *